US006815433B2

(12) United States Patent
Hansson et al.

(10) Patent No.: US 6,815,433 B2
(45) Date of Patent: Nov. 9, 2004

(54) COMPOSITION AND METHOD FOR THE TREATMENT OF DYSGLUCAEMIA

(75) Inventors: Henri Hansson, Helsingborg (SE); Mats Lake, Lidingo (SE); Kerstin Hansson, Lund (SE)

(73) Assignee: Metcon Medicin AB, Lindingo (SE)

( * ) Notice: Subject to any disclaimer, the term of this patent is extended or adjusted under 35 U.S.C. 154(b) by 0 days.

(21) Appl. No.: 10/002,417

(22) Filed: Oct. 25, 2001

(65) Prior Publication Data

US 2002/0094971 A1 Jul. 18, 2002

Related U.S. Application Data

(60) Provisional application No. 60/243,072, filed on Oct. 25, 2000.

(30) Foreign Application Priority Data

Oct. 25, 2000 (SE) .............................................. 0003877

(51) Int. Cl.⁷ ............................................. A61K 31/715
(52) U.S. Cl. ........................................ 514/57; 514/60
(58) Field of Search ...................................... 514/57, 60

(56) References Cited

U.S. PATENT DOCUMENTS

| | | | | |
|---|---|---|---|---|
| 5,360,614 A | | 11/1994 | Fox | 424/439 |
| 5,470,839 A | * | 11/1995 | Laughlin et al. | 514/53 |
| 5,545,410 A | | 8/1996 | Fox | 424/439 |
| 5,605,893 A | | 2/1997 | Kaufman | 514/60 |
| 5,843,921 A | | 12/1998 | Kaufman | 514/60 |
| 5,866,555 A | * | 2/1999 | Bell et al. | 514/60 |
| 6,316,427 B1 | * | 11/2001 | Axelsen et al. | 514/60 |
| 6,339,076 B1 | * | 1/2002 | Kaufman | 514/60 |

FOREIGN PATENT DOCUMENTS

WO    WO 95/24906    9/1995    ......... A61K/31/715

* cited by examiner

*Primary Examiner*—Kevin E. Weddington
(74) *Attorney, Agent, or Firm*—Young & Thompson

(57) ABSTRACT

Dysglucaemia is treated and/or prevented by the administration of granulated starch, enzymatically degraded and releasing reducing sugars at a rate, adjusted to the metabolism of the patient, suffering from dysglucaemia. For example nocturnal hypoglycaemia in diabetic patients is prevented by administering to said patients a granulate or tablets comprising granulated cornstarch, and preferably also heat treated cornstarch and a low calorie sweetener. The inventive granulation minimizes the available surface area and retards the enzymatic degradation of the cornstarch and ensures a controlled, e.g. a substantially linear release of reducing sugars, such as glucose, and a stable blood glucose level during several hours. The granulate or tablets are low in calories and contain no free sugar.

48 Claims, 5 Drawing Sheets

COMPOSITION AND METHOD FOR THE TREATMENT OF DYSGLUCAEMIA

CROSS REFERENCE TO RELATED APPLICATIONS

This application claims the benefit of U.S. Provisional Application No. 60/243,072, filed Oct. 25, 2000 and Swedish Application No. SE 0003877-8 filed Oct. 25, 2000.

The present invention concerns a method for long term prevention and/or treatment of dysglucaemia and/or for improved glycaemic control, for example the long term prevention of nocturnal and morning hypoglycaemia in diabetic patients, a composition for this purpose and a method for its production.

BACKGROUND OF THE INVENTION

Dysglucaemia is an overall definition, which in the present description and claims is meant to comprise all irregularities in blood glucose level in humans, both healthy persons and persons with a diagnosed disease, irrespective of these irregularities being chronic or temporary, caused by a metabolic disorder, a disease or by physical exercise, bad nutritional habits, medical treatment such as surgery, and desired or undesired pharmaceutical or chemical influences, such as pharmaceutical treatments or substance abuse.

Diabetes mellitus is a complex disorder of the carbohydrate, fat, and protein metabolism that is primarily a result of a relative or complete lack of insulin secretion by the beta cells of the pancreas or of defects of the insulin receptors. The various forms of diabetes are divided in several categories, the two most frequent being juvenile-onset diabetes or Type I insulin-dependent diabetes mellitus (IDDM) and adult-onset diabetes or Type II non-insulin-dependent diabetes mellitus (NIDDM). Both diseases, even when correctly diagnosed and medicated, require life-long medication, good patient compliance, a careful diet and frequent medical observation to avoid potentially serious sequelae.

One problem, frequently encountered by patients suffering from diabetes, is the nocturnal drop in blood glucose levels, hypoglycaemia, in mild cases resulting in morning dizziness and/or nausea. Occasionally the blood glucose level sinks so low during the night, or early in the morning, that the state of hypoglycaemia becomes severe, leading to unconsciousness or convulsions. Importantly, severe hypoglycaemia is more likely to occur at night, when the patient is asleep, rather than during the day, when the patient can feel the onset of hypoglycaemia and prevent it by eating carbohydrates, e.g. a lump of sugar or specific glucose tablets, energy gels or bars, marketed for diabetic patients.

Moreover, both mild (a blood glucose level about 2.4–4.0 mmol/l) and severe (less than 2.4 mmol/l) hypoglucaemia predisposes the patient to a condition known as hypoglycaemic unawareness, which in turn means that hypoglucaemia can occur more frequently and at any time of the day, due to attenuation of the typical warning symptoms of a declining blood glucose level, e.g. hunger, perspiration etc.

Notably, the incidence of hypoglycaemia is rapidly increasing as diabetic patients seek better control of their blood glucose levels, in order to avoid hyperglycaemia. An active life, involving exercise as prescribed for diabetics, also adds to the risk of hypoglycaemia unless the patient carefully controls his/her carbohydrate intake, insulin dosage and regularly monitors their blood glucose level.

There is presently no satisfactory therapeutic regime for the prevention of nocturnal and morning hypoglycaemia. Patients suffering from diabetes are often recommended to eat a light meal before bedtime, e.g. potato chips or cereals. This results in an almost instant peak in blood glucose, followed by a more or less rapid decline during the night. In order to guarantee a sufficient blood glucose level throughout the night, the initial level must be very high, bordering to the unhealthy. When attempting this kind of crude self-medication, the patients have difficulty finding the optimal dose and mix of carbohydrates, and over-eating tends to be the result. There is currently no medication available with an appropriate kinetic profile to counteract the effect of the night-time intermediate-acting insulin.

PRIOR ART

A method of treating diabetic hypoglycaemia by administration of uncooked cornstarch is described in W095/24906. According to this application, published in September 1995, the patient is given about 0.1 to 1.0 g starch per kg body weight, preferably about 0.25 to 0.5 g per kg body weight. Different dosage formulations are suggested, including a suspension of starch in milk, sustained release tablets and a snack bar, containing a total of 30 g carbohydrates, but having about ½ to ¼ of the carbohydrate in the form of uncooked cornstarch. Although containing "slow" carbohydrates in the form of cornstarch, this product contains considerable amounts of free sugar and fats, resulting both in an initially very high blood glucose peak, and in the intake of unnecessary calories in the form of fats and surplus carbohydrates. Further information concerning the sustained release tablets is not given, apart from a reference to well known techniques of tablet formulation.

U.S. Pat. No. 5,605,893 (Kaufman, F.) discloses a specific method of treating a diabetic patient and preventing hypoglycaemic episodes, said method consisting of administration to the patient of a therapeutic food composition comprising per serving or unit about 20–50 grams of nutrients, including about 5–15 g of slowly absorbed complex carbohydrate, preferably cornstarch;

about 7–19 g of rapidly absorbed complex carbohydrate;

about 5–20 g of protein; and about 3–7 g of fat, said composition being substantially free from simple sugars.

U.S. Pat. No. 5,843,921 (Kaufman, F.) discloses a therapeutic food composition for treatment of diabetic patients and preventing hypoglycaemic episodes, comprising per serving or unit about 20–50 grams of nutrients, including about 5–15 g of slowly absorbed complex carbohydrate, preferably cornstarch;

about 7–19 g of rapidly absorbed complex carbohydrate;

about 5–20 g of protein; and about 3–7 g of fat;

wherein the amount of simple sugars other than fructose in said composition is less than about 3 g per unit.

U.S. Pat. No. 5,866,555 (Bell, S. J. et al.) discloses a diabetic supplement bar for the treatment or prevention of night time hypoglycaemia in a diabetic patient, made by blending simple carbohydrates, proteins, lipids, complex carbohydrates, and any additional additives, and homogenising the mixture into a food bar. Sucrose is presented as the preferred source of simple carbohydrates, whereas uncooked cornstarch is the preferred source of complex carbohydrates. The final fat concentration of the product is high, from 2 to 40% by weight. The remaining ingredients are:

about 10–60% by weight sucrose;

about 1–25% by weight protein;

about 1–60% by weight complex carbohydrate.

The high fat content of the above products accounts—together with the naturally slow degradation of uncooked cornstarch—for the delayed glucose release, as fat delays gastric emptying, thereby slowing the rate at which nutrients enter the intestines and become digested.

Another product, available on the market under the trade mark NiteBite® (Optim Nutrition Inc.) contains three sources of glucose: sucrose, protein and uncooked cornstarch. These components are digested more or less consecutively and are claimed to deliver glucose into the blood during a period of 6 hours or more.

U.S. Pat. No. 5,545,410 discloses the coating of a core of a carbohydrate in a food or pharmaceutical grade coating such as stearic acid, hydrogenated or partially hydrogenated oils, calcium stearate, stearyl alcohol, wax etc. The claims of U.S. Pat. No. 5,545,410 mention sucrose, glucose, lactose, dextrins, monosaccharides, disaccharides, oligosaccharides, and polysaccharides, as well as pregelatinized starches, raw starches, and modified starches. A limitation is however that the coated core has a particle size from 30–1000 $\mu$m. The resulting product consists of individually coated particles or granulates thereof, the properties of the coating regulating the release of the core compound.

The related patent U.S. Pat. No. 5,360,614 discloses the above coated carbohydrated cores, further defining their size to the interval of 75–500 $\mu$m, and the coating as providing for the release of substantially all said metabolizable carbohydrate into the digestive system for one-half to four hours after ingestion.

The prior art compositions fail to provide an entirely satisfactory solution for long term treatments when all effects and consequences are taken into account. The sucrose included in some preparations can lead to initial hyperglycaemia and may additionally contribute to caries and tooth decay. The proteins, and in particular the fat included in some of the above preparations provide unnecessary additional calories to patients, who in many cases already battle with weight problems.

The objective of the present invention is thus to accurately and reliably regulate blood glucose levels in humans and prevent dysglucaemia, in particular long term prevention of dysglucaemia. This objective can be divided in the prevention of dysglucaemia in diabetic patients, and in particular the prevention of nocturnal dysglucaemia in diabetic patients.

Another related objective is to prevent nocturnal hypoglycaemia in diabetic patients and in particular in type 1 and type 2 diabetics on insulin medication.

A further problem is how to prevent and/or treat dysglucaemia in both healthy subjects, such as athletes, and in unhealthy, such as patients undergoing surgery, chemotherapy etc, and in particular diabetic patients undergoing medical treatment.

Further, it is desirable to make available a simple and yet reliable way of improving the glycaemic control or stabilising the oscillating blood sugar levels typical for diabetic patients, and avoiding both the high and low blood sugar levels, both conditions injurious to the health, especially when occurring repeatedly or for prolonged periods of time.

It is particularly desirable to make available a method and composition giving a controlled, delayed enzymatic digestion of the starch and preferably a substantially linear glucose release curve and thus guaranteeing a predetermined, stable and sufficient blood sugar level during at least 5 hours, preferably about 8 hours.

A practical problem encountered in pursuing the above objectives is how to make available a cornstarch composition having an agreeable taste and texture, suitable for daily consumption and life long treatment. This is not without significance, as a tasty product advances good compliance.

SUMMARY OF THE INVENTION

The present inventors have surprisingly found that the conversion of starch into sugar and in particular the enzymatic conversion of cornstarch into glucose, can be regulated or delayed in a controlled manner and adapted to the metabolism of the patient, without relying on the delaying effect of fat. Thus the blood sugar level can be held at a desired level, e.g. a level accurately adjusted to the metabolic needs of the patient, avoiding both peaks with the associated risk of hyperglycaemia, and low levels, and the corresponding risk of hypoglycaemia. Importantly, this can now be achieved without the administration of unnecessary surplus calories. Further, the present invention makes available a tasty and palatable product consisting substantially of native cornstarch.

The problems associated with the prior art products are solved, and the above objectives of the invention are achieved by a novel composition and a method comprising administering to the patient in question a starch product with minimised available surface area, such as a granulated and/or partially encapsulated starch, preferably native cornstarch. The method of treatment, the pharmaceutical composition itself and the process for its production are as disclosed in the attached claims.

SHORT DESCRIPTION OF THE DRAWINGS

The present invention will be described in closer detail in the following description, examples and enclosed drawings, in which FIG. 1 shows the in vitro degradation profiles for different compositions according to the invention, compared to the profile for untreated cornstarch;

Figure 4:
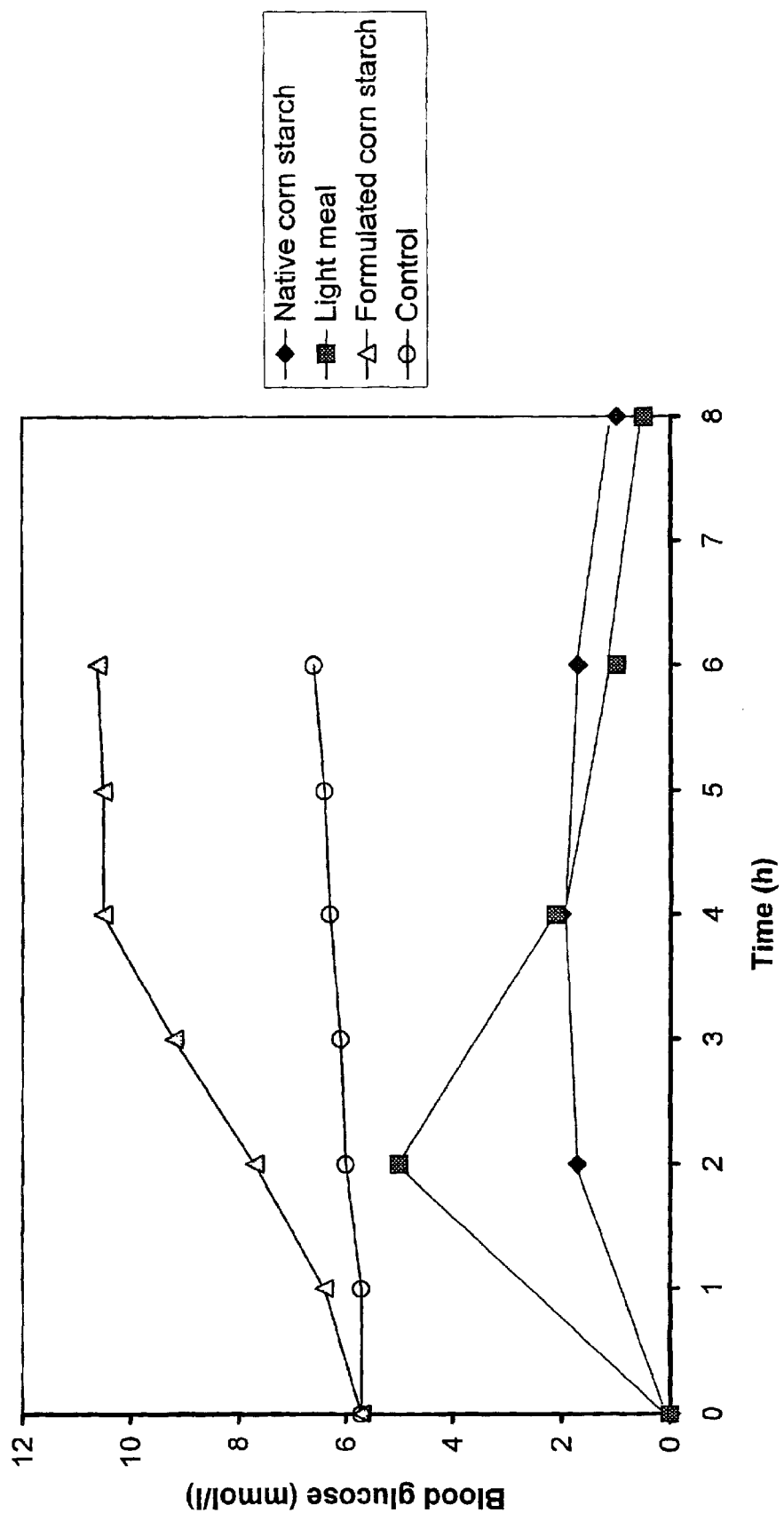
Figure 5:
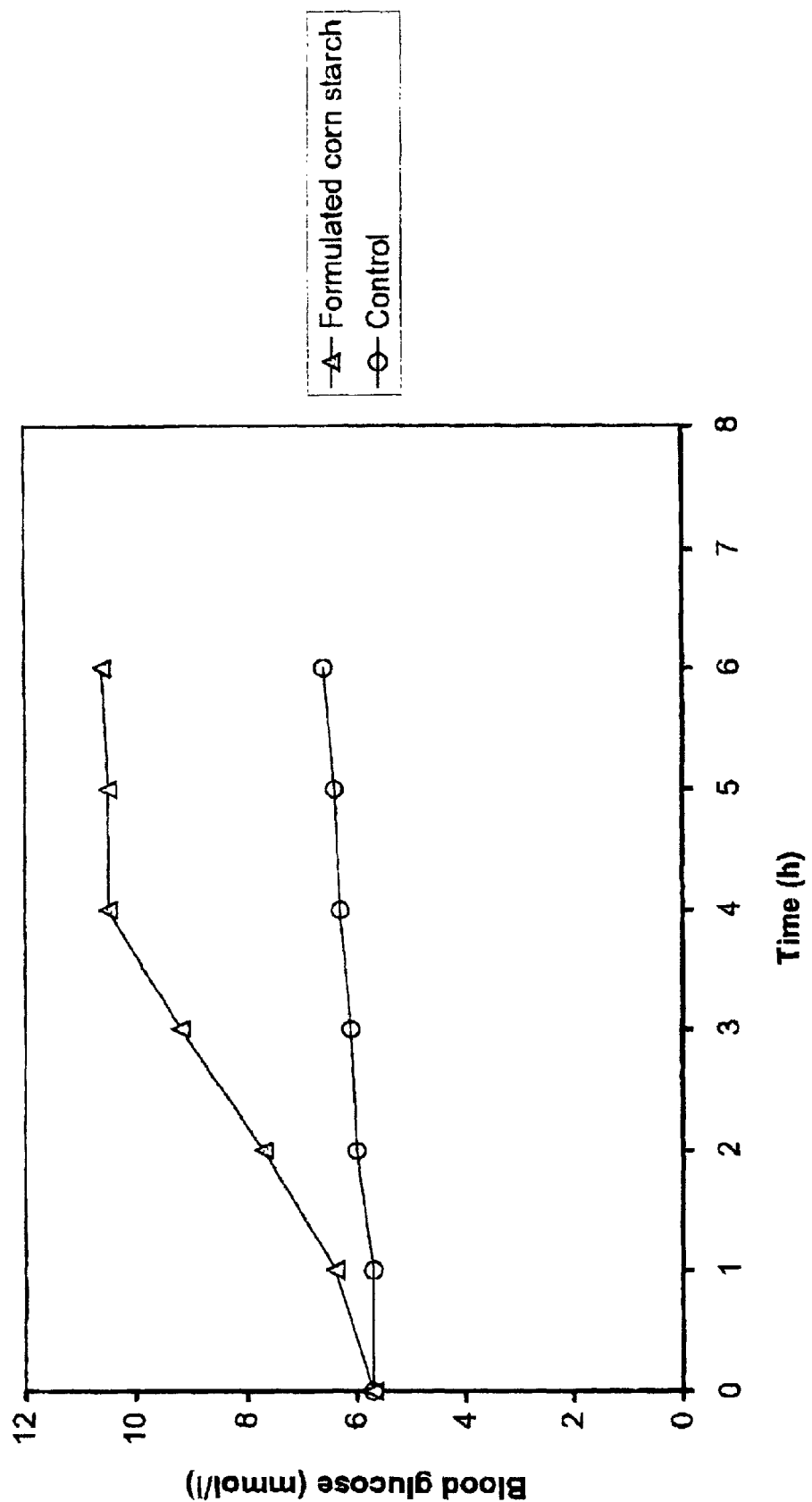

FIG. 4 shows the in vivo blood glucose contribution in a diabetic patient after intake of a light meal compared to native cornstarch; and FIG. 5 shows the in vivo blood glucose curve of a diabetic patient having taken the inventive composition, compared to control, excipients only, during ongoing insulin infusion according to the glucose clamp technique. The upper curve thus shows the contribution of the inventive composition.

DESCRIPTION

Starch is the main storage polysaccharide in plants, an important source of carbohydrates and an ingredient in food. More than half of the carbohydrates ingested by humans is starch. Starch also has many technical uses, accounting for large volumes of the starch produced. Examples include the use as a sizing agent in paper industry, a raw material and/or additive in the production of plastics, textiles etc. and as a carrier and bulk agent in pharmaceutical industry. Starch is also used as a non-adherence agent for surgical gloves. Apart from these purely technical uses, it is not know to the present inventors that native starch as such would have a purely therapeutic, internal use, nor that it would have constituted the active ingredient in a pharmaceutical composition, such as a tablet as disclosed in the present description and claims.

Pure starch, although theoretically a good source of glucose and free from surplus calories, is practically impossible to ingest. The starch powder itself lacks taste and feels extremely dry, chalky or sandy in the mouth. A suspension on the other hand, e.g. a suspension in water, tends to sediment quickly, and has a disagreeable taste and texture.

Cornstarch consists of granules sized 2–32 µm, mainly comprising two components, amylose and amylopectin. Amylose has a linear structure while amylopectin is branched. Both amylose and amylopectin consist of α-(1, 4)-linked glucose residues while amylopectin also has α-(1, 6)-linked glucose residues. The starch granules are insoluble in cold water and swell in warm. The swelling is reversible until the temperature reaches about 55 to 65° C. At this temperature the starch granules gelatinise and loose their crystalline structure.

The degradation of starch is catalysed by α-amylase, which in humans is present in the saliva and in the small intestine. The digestibility of starch, both in vivo and in vitro depends on the source of starch as well as its pre-treatment (e.g. native, fine/coarse, gelatinised or chemically modified). In the present description, claims and examples, the term "native starch" is used to define starch that has not been subjected to heat-treatment or chemical treatment. The term "native starch" thus comprises both the vegetable and/or plant seeds, kernels or grains, as well as mechanically treated fractions, such as the milled and sieved product, granules and flour.

The present inventors have now surprisingly found, that the enzymatic degradation of the starch in vivo can be regulated in an accurate and repeatable manner by minimising the surface area available to enzymatic action, preferably by granulating the starch granules with a substance, resulting in aggregated granules being at least partially encapsulated in the substance.

Suitable substances are non-toxic substances, suitable for ingestion, such as substances generally recognised as safe (GRAS) and approved for use in pharmaceutical applications and/or in food products. A non-exclusive list of suitable substances includes polymers such as gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

Tests conducted in vitro, have shown that a controlled enzymatic digestion and a substantially linear release profile is achieved when the amount of reducing sugars is plotted against time. Test conducted in vivo, using healthy volunteers, have shown that a modulated release profile is achieved. This makes it possible to achieve a long term delivery of reducing sugars, adjusted in level and duration to the metabolic needs of the patient. An additional in vivo test, conducted on a diabetic patient, confirms the performance of the inventive composition and the feasibility of the inventive method. This test was performed after the priority date, but before the international filing date.

The present invention makes available a method and composition for the long term prevention and/or treatment of dysglucaemia, e.g. the prevention of nocturnal and/or morning hypoglycaemia in patients suffering from diabetes, including both IDDM and NIDDM, wherein a predetermined amount of starch is administered to the patient in granulated and at least partially encapsulated form, most preferably in the form of tablets, which granulation delays the enzymatic degradation of the starch into reducing sugars, such as glucose. The starch is preferably native cornstarch.

The present invention also makes available a method and composition for the prevention of dysglucaemia in situations, where the blood glucose level is disturbed or altered by exercise, pharmaceutical or surgical therapy, by a disease or a syndrome, involving multiple diseases or metabolic disorders. Examples include athletes, patients weakened by chemotherapy, fasting patients and patients suffering from diseases or disorders disturbing or altering the sugar metabolism, or patients undergoing treatment of such and other diseases or disorders. The method is characterised in that a predetermined amount of starch is administered to the patient in granulated and at least partially encapsulated form, preferably in the form of tablets, which granulation delays the enzymatic degradation of the starch into reducing sugars, such as glucose. The starch is preferably native cornstarch.

The present invention also makes available a method and composition for improved glycaemic control, i.e. for stabilising the blood sugar levels and avoiding the oscillation between unhealthy high and low blood sugar levels. Lack of glycaemic control is associated inter alia with microvascular damage, such as diabetic retinopathy, and diabetic ketoacidosis or so called diabetic coma.

The present invention further makes available a composition for controlled release of reducing sugars, e.g. glucose, wherein said composition contains granulated and at least partially encapsulated starch, a low calorie sweetener and optionally also unsaturated fat. The starch is preferably native cornstarch.

According to one embodiment of the invention, the native starch is granulated with and at least partially encapsulated in a substance chosen among non-toxic substances, suitable for ingestion, such as substances generally recognised as safe (GRAS) and approved for use in pharmaceutical applications and/or in food products. A non-exclusive list of suitable substances includes polymers such as gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

Preferably the substance is chosen among guar gum and ethyl cellulose, most preferably ethyl cellulose.

According to the invention, the enzymatic degradation is delayed to an extent resulting in a controlled and substantially linear release of reducing sugars, e.g. glucose, accurately adapted to the metabolism of the patient for more than 4 hours, preferably more than 6 hours, most preferably about 8 hours or longer.

According to one embodiment, the composition comprises starch in two forms; a first amount of native starch, and a second amount of heat treated starch. Preferably the second amount of heat treated starch is about 0.1 to 15% by weight of the total amount of starch, preferably about 5% by weight.

According to a preferred embodiment the heat treated and un-encapsulated starch is in the form of flakes of baked starch having a size in the interval of about 0.5–1.0 mm.

According to one embodiment, the inventive composition for controlled release of glucose comprises the following ingredients:
about 60–90% by weight native cornstarch encapsulated in a substance,
optionally about 0.1–15% by weight heat treated cornstarch in the form of flakes;
about 5–25% by weight low calorie sweetener, e.g. isomalt, sorbitol, xylitol, or the like, preferably isomalt.

According to another embodiment, the inventive composition for controlled release of glucose comprises the following ingredients:
about 60–90% by weight native cornstarch encapsulated in a substance,
optionally about 0.1–15% by weight heat treated cornstarch in the form of flakes;
about 0.1–10%, preferably 0.1–5% by weight unsaturated fat;
0.01–25% by weight low calorie sweetener, e.g. isomalt, sorbitol, xylitol, saccharin, or the like, preferably isomalt.

Preferably the heat treated flakes have a size in the interval of 0.5 to 1.0 mm and the unsaturated fat is olive oil. The composition may further contain optional additives, such as additives giving the final product its colour and taste.

The heat treated starch may be added in the form of baked flakes, which give the product a crispy texture and a pleasant taste. Flakes suitable for this purpose are made of a mixture of cornstarch, water, sodium chloride and sweetener. The flakes are heated above gelatinisation temperature and subsequently dried at about 90° C. The dried flakes are milled and sieved. Flakes in the interval of about 0.5–1.0 mm are then mixed with the granulated and at least partially encapsulated cornstarch.

Preferably the substance which encapsulates the starch is chosen among non-toxic substances, suitable for ingestion, such as substances generally recognised as safe (GRAS) and approved for use in pharmaceutical applications and/or in food products. A non-exclusive list of suitable substances includes polymers such as gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

Preferably the substance is chosen among guar gum and ethyl cellulose, most preferably ethyl cellulose.

According to a preferred embodiment, an organic acid is added to the inventive composition. The organic acid is preferably one of ascorbic acid, tartaric or citric acid.

The inventive composition may further comprise minor amounts of technical additives, such as conventional tabletting agents, lubricants and glidants.

The present invention discloses a method for production of a composition for the controlled delayed degradation of starch, wherein the method comprises the following steps granulation and at least partial encapsulation of native cornstarch in a substance which delays the degradation, wet sieving and drying of the encapsulated granules, adding a low calorie sweetener and an organic acid, and pressing the mixture into tablets.

As one embodiment, the present invention further discloses a method for production of a composition for the delayed degradation of starch, wherein the method comprises the following steps granulation and at least partial encapsulation of native cornstarch in a substance which delays the degradation, wet sieving and drying of the encapsulated granules, mixing the granules with heat treated flakes of cornstarch, adding a low calorie sweetener, an organic acid and unsaturated fat to the mixture, and pressing the mixture into tablets.

The tablets are then packaged according to conventional methods, in a package suitable for storage, delivery and sale. Optionally, the granulate is not pressed into tablets but weighed and packaged according to conventional methods, in a package suitable for storage, delivery and sale.

The substance which delays the degradation is chosen among non-toxic substances, suitable for ingestion, such as substances generally recognised as safe (GRAS) and approved for use in pharmaceutical applications and/or in food products. A non-exclusive list of suitable substances includes polymers such as gum arabicum, potassium alginate, guar gum, methyl cellulose, ethyl cellulose; liquid oils, liquid and hard fats and waxes, such as paraffin, hydrogenated cottonseed oil, beeswax, and carnauba wax. Preferably the substance is chosen among guar gum and ethyl cellulose, most preferably ethyl cellulose.

The heat treated starch may be added in the form of baked flakes, which give the product a crispy texture and a pleasant taste. Flakes suitable for this purpose are made of a mixture of cornstarch, water, sodium chloride and sweetener. The flakes are heated above gelatinisation temperature and subsequently dried at about 90° C. The dried flakes are milled and sieved. Flakes in the interval of about 0.5–1.0 mm are then mixed with the granulated and at least partially encapsulated cornstarch before tablet pressing.

According to a preferred embodiment, an organic acid is added to the mixture before tablet pressing, the organic acid being chosen among ascorbic acid, tartaric acid and citric acid, preferably tartaric acid. An organic acid has the additional advantage of stimulating the secretion of saliva. This is especially advantageous as pure starch and products with a high starch content have a dry and chalky or sandy mouth feel and bland or even disagreeable taste.

The product according to the present invention is delivered in the form of a granulate, or preferably in the form of pressed cakes or tablets. The pressed cakes or tablets are preferably produced with grooves or notches for easy division into even sized fractions.

According to one embodiment of the invention, a saturated or preferably unsaturated fat is added to the granulate before tablet pressing. Preferably an unsaturated fat is used, and most preferably olive oil, added in about 0.1–5% by weight for tabletted products, and 0.1–10% by weight for granulates.

According to one embodiment of the invention a low calorie sweetener is added, and preferably saccharin, isomalt or xylitol is used as the sweetener. Xylitol imparts a cooling sensation because of its endothermic dissolution.

A specific advantage of the method and composition of the present invention is that practically all of the starch, contained in the ingested dose, is converted to reducing sugars, mainly glucose. Thus the amount of glucose can be accurately calculated and the dose optimised for each patient, e.g. by producing tablets of different size or by ordinating the patient to take a prescribed number of tablets. Further, a minimum of surplus calories are administered to the patient.

A particular advantage of the present composition and method is that the release rate and the content of reducing sugars can be accurately controlled and adjusted to the needs of the specific patient group, specific application or medical situation, and adjusted to the metabolism of the patient or patient. A method and product according to the invention makes possible an exact and reliable dosage and ease of use.

Another advantage of the composition according to the present invention is that undigested starch is prevented from reaching the colon, where it would be digested by bacteria, resulting in the formation of gas, especially in the colon.

Another advantage is that—for the first time known to the inventors-a substantially pure starch composition has been formulated as a product with agreeable taste and mouthfeel. As touched upon above, the sensory qualities of a medical product have importance for compliance.

EXAMPLES

In vitro Degradation Tests

The tested formulations were prepared using a high shear mixer (Donsmark QMM-II) and tablets pressed with a hydraulic single press (Compac DP6-B2) or with a rotary tablet press (Korsch Pharmapress PH-106). All formulations were based on native cornstarch (Maizena, Bestfoods Nordic AB). Cornstarch and different excipients were dry mixed in a granulator and agglomerated with water or ethanol as granulation fluid, depending on the solubility of the granulation substance used. The dry granulate was pressed into tablets.

In order to study the enzymatic degradation of starch in vitro, a novel analytical method was developed, and is the object of co-pending application PCT/SE01/02298. According to this method, the degradation resistance of starch by the action of α-amylase is measured as the concentration free sugar in a starch suspension incubated at 37° C. after the addition of enzyme. Samples are taken at regular intervals and the reducing sugars, e.g. glucose and maltose, are reacted with a reagent consisting of a filtered 3,5-dinitro salicylate solution in aqueous NaOH. The formed colour is determined spectrophotometrically by scanning over the wave length interval of 450–500 nm, detecting the absorption maximum. Enzymatic degradation is then plotted as sugar concentration as a function of the incubation time.

Example 1

Cornstarch Granulated with Potassium Alginate (10%) Compared to Free Cornstarch

Method of Production: Native cornstarch (Maizena, Best-foods Nordic AB) was mixed in a high shear mixer with potassium alginate (10% by weight, Food grade, Danisco) and water added as granulation fluid. The granules were wet sieved through a 1 mm sieve and dried in a forced hot air oven (Fermaks) at 35–40° C. The dried granulate was sieved through a 1 mm sieve and collected on a 0.5 mm sieve. A small amount of fat was added [5, 8 and 10% olive oil (food grade, Zeta), or 5, 10 and 20% Akosupp 10 (Karlshamns AB)]. The granulate and/or tablets were tested in vitro according to the method described below, and in vivo according to the method described further below, in connection with the in vivo tests.

Method of Analysis: A reagent was made by dissolving 3,5-dinitro salicylate (2.00 g, Aldrich) in aqueous NaOH (70 ml, 1 M). Optionally, the mixture is heated in order to expedite the formation of a clear solution. Upon cooling, water is added to 100 ml. The reagent solution is stored in a dark place and filtered through a 0.45 μm filter before use, in order to remove possible precipitates.

The reagent solution was added in equal amounts (2 ml) in test tubes marked "control", "zero", "5 min", "10 min", "20 min", "30 min", "45 min", "1 h", "1.5 h", "2 h", "2.5 h", "3 h", "3.5 h", and "4 h". The test tubes were placed in an ice bath awaiting the analysis.

A buffer solution (pH 6.6) was made by mixing $KH_2PO_4$ (250.0 ml, 0.20 M, Sigma) and NaOH (89.0 ml, 0.20 M) and adding water to a total volume of 1000 ml. NaCl (0.58 g, Riedel-de Haën) was then added to produce a chloride concentration of 0.01 M.

A defined amount of starch to be investigated is suspended in the above buffer and placed in the degradation bath. The degradation bath is kept at a temperature of 37° C. +0.5° C. and stirred at a speed of 50 rpm.

An amount corresponding to 15 000 α-amylase (Type VI-B from porcine pancreas, Sigma) is measured and suspended in buffer. Before addition of the enzyme solution, a sample of the degradation bath is taken in order to determine the sugar concentration at "time zero". The sample is filtered through a 0.8 μm filter and an aliquot (2 ml) is pipetted to the test tube marked "zero". The same filter can be used throughout the series. The sample is boiled momentary (5 min) and placed in an ice-bath. Following this, the enzyme solution is added to the degradation bath and the time registered. Samples are then taken at predetermined intervals, such as the times indicated on the test tubes. The control is prepared by boiling reagent (2 ml) and water (2 ml) during 5 min and placing the sample in an ice-bath.

For each sample, the absorption is scanned in the interval 450–500 nm and the peak height registered for each absorption maximum. In order to determine the concentration free sugars (FS0) in the native starch, the absorbance of the sample "zero" is measured against a background of water and reagent, the control sample. Both samples and control are diluted by adding 11.6 ml water to 400 μl sample. The reacted and diluted sample solution is not stable (the reading falling 0.1 to 0.2 absorbancy units during 3 hours) so all samples are diluted slightly prior to the UV-spectrophotometric analysis.

Example 2

Cornstarch Granulated with Potassium Alginate (20%) Compared to Free Cornstarch

Native cornstarch was granulated with 20% by weight potassium alginate and analysed as described in Example 1.

Example 3

Cornstarch Granulated with Guar Gum (20%) Compared to Free Cornstarch

Native cornstarch was granulated with 20% by weight guar gum (Scanpharm A/S) and analysed as described in Example 1.

Example 4

Cornstarch Granulated with Ethyl Cellulose Compared to Free Cornstarch

Native cornstarch was granulated with 18% by weight ethyl cellulose (Dow Chemical Co.) and analysed as described in Example 1.

Figure 1:
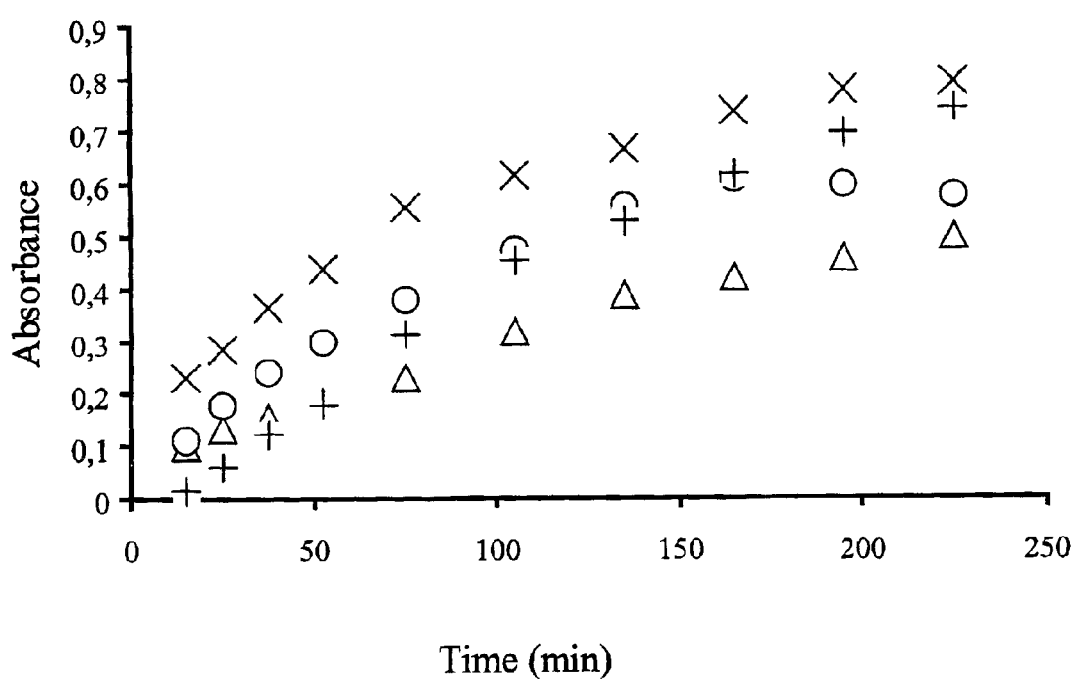

The results of the in vitro degradation tests are shown in FIG. 1, where the values for cornstarch encapsulated in ethyl cellulose (10%) are marked with the symbol (○), cornstarch encapsulated in ethyl cellulose (20%) with (Δ), cornstarch encapsulated in guar gum (20%) being marked with (9) and the values for untreated cornstarch being marked (6).

In vivo Tests

The blood glucose response was measured by the standard technique in 4 healthy, lean volunteers (age 35 to 45 years) with normal glucose tolerance. According to the "golden standard" of this technique, each substance was studied twice in each volunteer, and the mean value was calculated. The substances were tested in randomised order, at least one day apart. Moreover, the testing was performed under strictly standardised conditions. The subjects came to the laboratory in the morning, fasted for 10 hours. Physical activity was avoided right before and during the test. The test subjects were allowed to drink about 2 dl liquid, free from carbohydrates (water, tea or coffee) twice during the test; at 0 and 3 hours.

Figure 2:
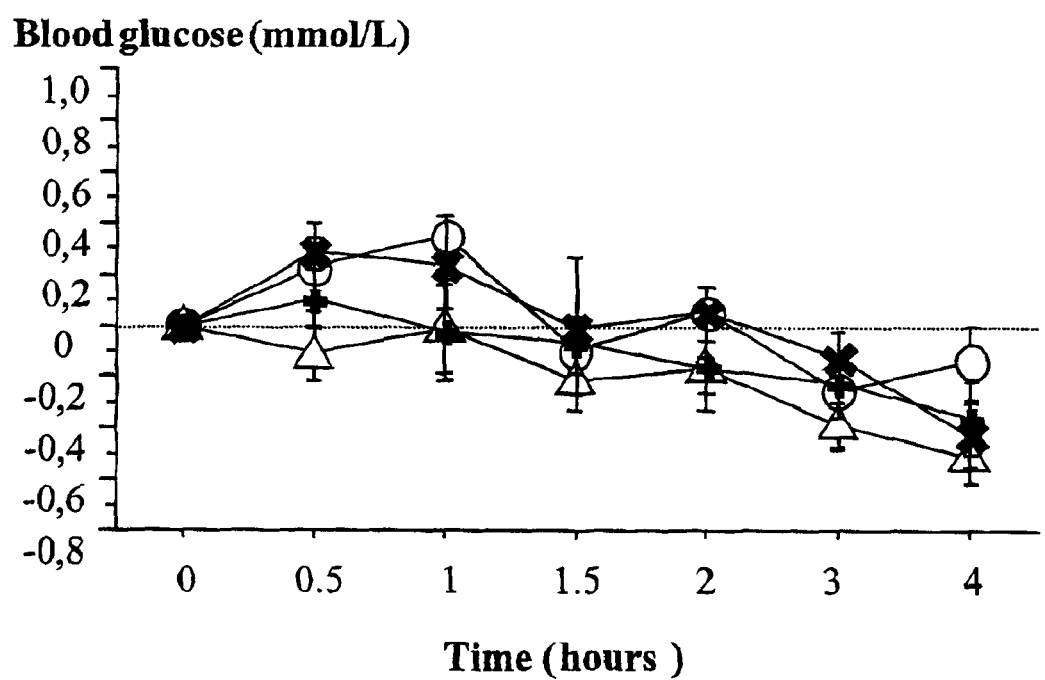
FIG. 2 shows the average fasting and postprandial blood glucose levels in healthy, fasting volunteers, after ingestion of 4 different compositions according to the invention.
Figure 3:
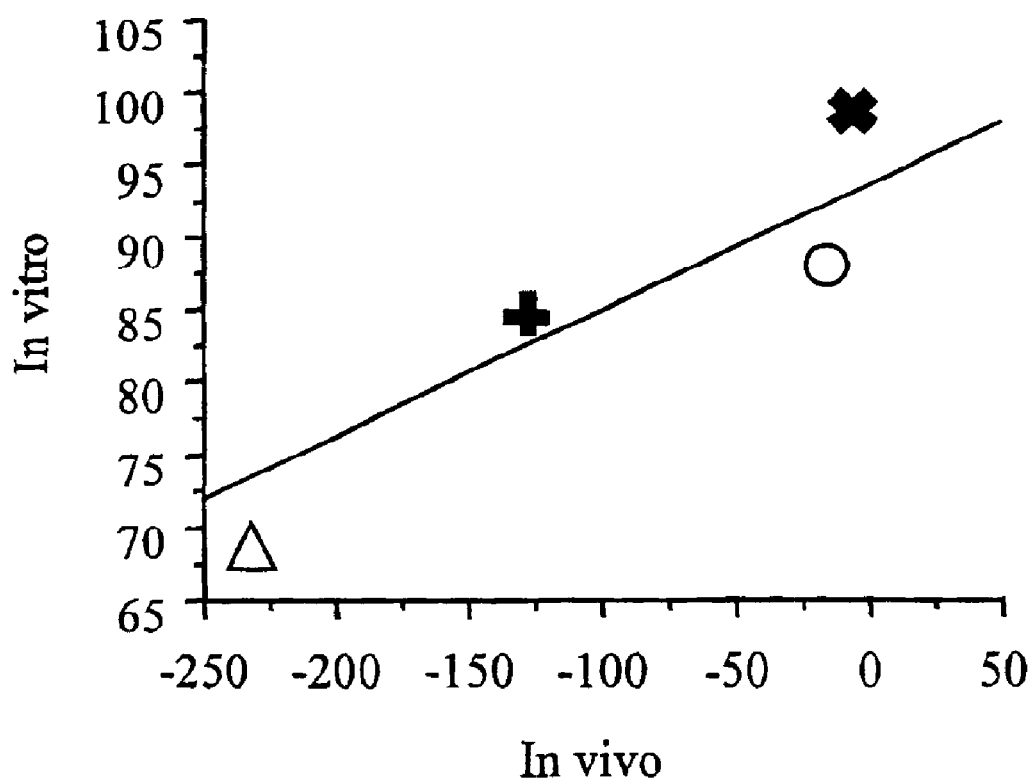
FIG. 3 shows the correspondence between rates of digestion/degradation as measured by in vivo and in vitro techniques.

The capillary blood glucose level was determined in capillary blood samples (obtained by finger pricking) using a Glucometer DEX (Bayer Diagnostica AB) following the standard procedures for glucose measurements. At baseline, three consecutive blood glucose determinations were performed to ensure a stable baseline at time 0 hours. Thereafter the test substance (20.0 g) was ingested together with a standardised amount of water within 5 minutes. All liquids were carefully weighed and the same amounts ingested at each occasion to avoid variations in transit time through the gastrointestinal tract. The blood glucose determination was repeated at 0.5, 1.0, 1.5, 2.0, 3.0, and 4.0 hours. The average results for the test subjects are shown in FIG. 2. The correspondence between rates of digestion as measured by in vivo (4 h blood glucose response, ((mmol/l min)*100) and in vitro (as described in Example 1) techniques is shown in FIG. 3.

Example 5

In vivo Effect of Cornstarch Granulated with Ethyl Cellulose (10%)

The test subjects measured their initial blood glucose after 10 hours of fasting, whereupon they ingested an exactly measured amount of a formulation of cornstarch granulated with and partially encapsulated in ethyl cellulose (10%), manufactured according to the method presented in Example 1 above. Blood glucose was then measured at 0.5, 1.0, 1.5, 2.0, 3.0, and 4.0 hours. The average result for all test subjects are presented in FIG. 2, the values for cornstarch encapsulated in ethyl cellulose (10%) being marked with (○).

Example 6

In vivo Effect of Cornstarch Granulated with Ethyl Cellulose (20%)

The test subjects measured their initial blood glucose after 10 hours of fasting, whereupon they ingested an exactly measured amount of a formulation of cornstarch encapsulated in ethyl cellulose (20%), manufactured according to the method presented in Example 1 above. Blood glucose was then measured at 0.5, 1.0, 1.5, 2.0, 3.0, and 4.0 hours. The average result for all test subjects are presented in FIG. 2, the values for cornstarch encapsulated in ethyl cellulose (20%) being marked with (Δ).

Example 7

In vivo Effect of Cornstarch Granulated with Guar Gum (20%)

The test subjects measured their initial blood glucose after 10 hours of fasting, whereupon they ingested a formulation of cornstarch encapsulated in guar gum (20%) manufactured according to the method presented in Example 1 above. Blood glucose was then measured at 0.5, 1.0, 1.5, 2.0, 3.0 and 4.0 hours. The average result for all test subjects are presented in FIG. 2, the values for cornstarch encapsulated in guar gum (20%) being marked with (9).

Example 8

In vivo Effect of Untreated Cornstarch

The test subjects measured their initial blood glucose after 10 hours of fasting, whereupon they ingested native, untreated cornstarch (Maizena, Bestfoods Nordic AB). Blood glucose was then measured at 0.5, 1.0, 1.5, 2.0, 3.0, and 4.0 hours. The average result for all test subjects are presented in FIG. 2, the values for untreated cornstarch being marked (6).

The in vivo results clearly show that a marked effect is achieved with the formulations according to the invention, compared to untreated cornstarch. Most notably, the initial glucose peak appearing at 0.5, 1.0 and 1.5 hours after ingestion of untreated cornstarch, is entirely absent for the guar gum encapsulated cornstarch.

Clinical Trials

Example 10

Comparative Tests Performed with Diabetic Patients

Study design: The 16 patients in the study will receive the inventive composition in tablet form (MM005) in different single doses, 5, 10 and 20 g, respectively, at three different occasions and the control (excipients only) at one occasion.

Establishment of baseline (control occasion): The subjects come to the laboratory in the morning in the fasting state and without having taken their regular morning insulin dose. With the help of a slow i.v. infusion of insulin, combined with a glucose infusion, the blood glucose level will be stabilised at 5.5 to 6.5 mmoles/l. The insulin will be administrated by an infusion rate, aiming at giving a blood insulin concentration of 15–20 mU/l. The glucose concentration will be locked by customary clamp technique, where blood sugar is measured every $5^{th}$ minute for 1 hour and the glucose infusion rate is adjusted if necessary to give the desired blood glucose concentration. Thereafter the control medication is given and the glucose clamp continued for 6 hours. The amount of glucose administrated during each hour will be used at the three subsequent test occasions. The objective is to establish a reference baseline for evaluation of doses.

Dose testing: The sequence of the subsequent three test occasions, i.e. for the three different doses of the investigational drug, will be randomised. At least one week should pass between test occasions. Every test day will be started by glucose and insulin infusion for 1 hour as described above. Thereafter the investigational drug is administrated orally as a single dose and the glucose infusion is continued so that the amount of given glucose during each hour corresponds to the amount given on day 1 (control occasion). During the three test days blood samples are withdrawn every $10^{th}$ minute during the first 6 hours of the experiment for glucose determination, and also every $60^{th}$ minute for insulin determination. The subject will be asked to return within 1–4 weeks for a new test.

Dose: The doses are 5 g, 10 g, and 20 g cornstarch, i.e. 3, 6 and 12 tablets. The dose is taken once a day, in the morning, as a single dose.

Drug administration: The formulated cornstarch is administrated orally as chewing tablets formulated according to the invention, together with 250 ml of water.

Discussion of Study Design: The aim of this study is to evaluate the increase in glucose levels following intake of three cornstarch doses (5, 10, 20 g) as well as the kinetic profile compared to a control period with inactive medication (excipients only).

This is important since the medication is to be used to prevent hypoglycemia, in particular nocturnal hypoglycemia. This usually occurs at between 02 and 04 in the morning.

There is currently no medication available with an appropriate kinetic profile to counteract an excessive effect of the night-time intermediate-acting insulin. Thus, diabetic subjects usually ingest food when they have measured low glucose levels at bedtime. However, very high early night-time glucose levels are necessary to provide a sufficient "buffer" at 02–04 o'clock in the morning. Thus, a medication which provides such an effect should be an important therapy in diabetes.

The doses chosen are within the range calculated to be required to counteract the effect of an excessive nocturnal insulin dose.

The use of a control medication (excipients only) provides a background which makes it possible to evaluate the glucose-releasing property of the active medication. The number of subjects included in the study has been calculated to give enough power to safely evaluate the glucose-releasing profile.

The subjects should not have any clinically significant manifestations of the specific diabetic microvascular disorders.

The subjects will be given glucose if the blood glucose levels drop below 3.5 mM, and the test will be discontinued on that day.

The first data available from the clinical studies show that the inventive composition is capable of stabilising the blood glucose over a period of at least 6 hours, and that the enzymatic degradation of starch/conversion into glucose exhibits a substantially linear behaviour.

In FIG. 4, the glucose contribution of a light meal (v), is compared to that of native cornstarch (♦). The benefits of native cornstarch are clearly visible from the diagram. The native cornstarch formulation totally lacks the initial glucose peak, and gives a steady contribution still after 8 hours, with the trend of the curve indicating a considerably longer effect than for that accountable to a light meal.

See also FIG. 5 which shows the glucose curve of a diabetic patient having eaten the inventive composition (Δ), compared to control, excipients only (○). The results display a pronounced effect of the inventive composition still after 6 hours, the trend of the curve indicating that the effect most probably lasts even longer. These tests were performed after the priority date, but before the international filing date.

In organoleptic tests, the test subjects described the formulations according to the present invention as "tasty", "crispy" and "easy to swallow".

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. A method for the prevention of dysglucaemia in a patient, the method involving a minimal supply of calories, characterized in that native cornstarch is administered orally to said patient in granulated form having a reduced surface available for enzymatic degradation, which granulation delays the enzymatic degradation of the starch into reducing sugars to a duration and level, adjusted to the metabolism of the patient.

2. A method for the long term prevention of nocturnal and/or morning hypoglycaemia in patients suffering from insulin dependent diabetes (IDDM) wherein a native cornstarch is administered orally to the patient in granulated form, which granulation delays the enzymatic degradation of the starch into reducing sugars to a duration and level, adjusted to the metabolism of the patient.

3. A method for effective glycaemic control in diabetic patients, the method involving a minimal supply of calories, characterized in that native cornstarch is administered orally to the patient in granulated form, which granulation delays the enzymatic degradation of the starch into reducing sugars to a duration and level, adjusted to the metabolism of the patient.

4. The method according to claim 1, characterized in that said patients are patients scheduled to undergo surgical or invasive medical treatment.

5. The method according to claim 1, characterized in that said patients are diabetic patients scheduled for surgical or invasive medical treatment.

6. The method according to claim 1, characterized in that said patients are suffering from a chronic disease selected from the group consisting of viral infections, liver disease, hepatitis, alcohol abuse, cancer, HIV, AIDS, and a combination thereof.

7. The method according to claim 1, characterized in that said patients are patients on post-operative medication, having undergone surgical or invasive treatment.

8. The method according to claim 4, characterized in that the treatment is given in conjunction to insulin treatment.

9. The method according to claim 5, characterized in that the treatment is given in conjunction to insulin treatment.

10. The method according to claim 6, characterized in that the treatment is given in conjunction to insulin treatment.

11. The method according to claim 7, characterized in that the treatment is given in conjunction to insulin treatment.

12. The method according to claim 1, characterized in that said patients are athletes training or participating in an endurance sport.

13. The method according to claim 2, characterized in that said patients are athletes training or participating in an endurance sport.

14. The method according to claim 3, characterized in that said patients are athletes training or participating in an endurance sport.

15. The method according to claim 4, characterized in that said patients are athletes training or participating in an endurance sport.

16. The method according to claim 5, characterized in that said patients are athletes training or participating in an endurance sport.

17. The method according to claim 6, characterized in that said patients are athletes training or participating in an endurance sport.

18. The method according to claim 7, characterized in that said patients are athletes training or participating in an endurance sport.

19. The method according to claim 8, characterized in that said patients are athletes training or participating in an endurance sport.

20. The method according to claim 12, characterized in that said endurance sport is selected from the group consisting of long distance running, long distance skiing or long distance skating.

21. The method according to claim 1, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

22. The method according to claim 2, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

23. The method according to claim 3, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

24. The method according to claim 4, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

25. The method according to claim 5, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

26. The method according to claim 6, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

27. The method according to claim 7, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

28. The method according to claim 8, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

29. The method according to claim 12, characterized in that the starch is encapsulated in a substance selected from the group consisting of gum arabicum, potassium alginate, guar gum, methyl cellulose, ethyl cellulose; liquid oils, liquid and hard fats and waxes, such as paraffin, hydrogenated cottonseed oil, beeswax, and carnauba wax.

30. The method according to claim 1, characterized in that the starch is encapsulated in ethyl cellulose.

31. The method according to any one of claim 2, characterized in that the starch is encapsulated in ethyl cellulose.

32. The method according to claim 3, characterized in that the starch is encapsulated in ethyl cellulose.

33. The method according to claim 4, characterized in that the starch is encapsulated in ethyl cellulose.

34. The method according to any one of claim 5, characterized in that the starch is encapsulated in ethyl cellulose.

35. The method according to claim 6, characterized in that the starch is encapsulated in ethyl cellulose.

36. The method according to claim 7, characterized in that the starch is encapsulated in ethyl cellulose.

37. The method according to claim 8, characterized in that the starch is encapsulated in ethyl cellulose.

38. The method according to claim 12, characterized in that the starch is encapsulated in ethyl cellulose.

39. The method according to claim 1, characterized in that the enzymatic degradation is delayed to an extent resulting in a linear release of reducing sugars for more than 4 hours.

40. The method according to claim 2, characterized in that the enzymatic degradation is delayed to an extent resulting in a linear release of reducing sugars for more than 4 hours.

41. The method according to claim 3, characterized in that the enzymatic degradation is delayed to an extent resulting in a linear release of reducing sugars for more than 4 hours.

42. The method according to claim 4, characterized in that the enzymatic degradation is delayed to an extent resulting in a linear release of reducing sugars for more than 4 hours.

43. The method according to claim 5, characterized in that the enzymatic degradation is delayed to an extent resulting in a linear release of reducing sugars for more than 4 hours.

44. The method according to claim 6, characterized in that the enzymatic degradation is delayed to an extent resulting in a linear release of reducing sugars for more than 4 hours.

45. The method according to claim 7, characterized in that the enzymatic degradation is delayed to an extent resulting in a linear release of reducing sugars for more than 4 hours.

46. The method according to any one of claim 8, characterized in that the enzymatic degradation is delayed to an extent resulting in a linear release of reducing sugars for more than 4 hours.

47. The method according to claim 12, characterized in that the enzymatic degradation is delayed to an extent resulting in a linear release of reducing sugars for more than 4 hours.

48. A method for treating patients suffering from or at risk of suffering from dysglucaemia, comprising administering orally to said patient in need thereof an effective amount of native cornstarch in granulated form having a reduced surface available for enzymatic degradation, wherein the granulation delays the enzymatic degradation of the starch into reducing sugars to a duration and level, adjusted to the metabolism of the patient.

* * * * *